(12) United States Patent
Giszter (10) Patent No.: US 9,480,409 B2
(45) Date of Patent: Nov. 1, 2016

(54) SENSING PROBE COMPRISING MULTIPLE, SPATIALLY SEPARATE, SENSING SITES

(71) Applicant: Drexel University, Philadelphia, PA (US)

(72) Inventor: Simon F. Giszter, Havertown, PA (US)

(73) Assignee: Drexel University, Philadelphia, PA (US)

( * ) Notice: Subject to any disclaimer, the term of this patent is extended or adjusted under 35 U.S.C. 154(b) by 620 days.

(21) Appl. No.: 13/784,200

(22) Filed: Mar. 4, 2013

(65) Prior Publication Data
US 2013/0211222 A1 Aug. 15, 2013

Related U.S. Application Data (63) Continuation of application No. 12/967,878, filed on Dec. 14, 2010, now Pat. No. 8,639,311, which is a continuation-in-part of application No. 12/065,697, filed as application No. PCT/US2006/035028 on Sep.

(Continued)

(51) Int. Cl.
*A61B 5/04* (2006.01)
*G01D 21/00* (2006.01)
*A61B 5/00* (2006.01)

(52) U.S. Cl.
CPC ........... *A61B 5/04001* (2013.01); *G01D 21/00* (2013.01); *A61B 5/40* (2013.01); *A61B 5/6868* (2013.01); *A61B 5/72* (2013.01)

(58) Field of Classification Search
CPC ............ A61B 5/04001; A61B 5/0476–5/048; A61B 5/0478; A61B 5/40; A61B 5/4005–5/4052; A61B 5/4058–5/4094; A61B 5/6847; A61B 5/6868; A61B 5/6877; A61B 5/72

USPC ......................................... 600/378, 544–545
See application file for complete search history.

(56) References Cited

U.S. PATENT DOCUMENTS

| | | |
|---|---|---|
| 4,506,673 A | 3/1985 | Bonnell |
| 5,057,092 A | 10/1991 | Webster, Jr. |

(Continued)

FOREIGN PATENT DOCUMENTS

| | | |
|---|---|---|
| WO | WO 01/17451 | 3/2001 |
| WO | WO 2008/002654 | 1/2008 |

OTHER PUBLICATIONS

Jung et al. "Imaging Brain Dynamics Using Independent Component Analysis", Proceedings of the IEEE Jul. 2001; 89 (7) pp. 1107-1122 (2001).*

(Continued)

*Primary Examiner* — Lee S Cohen
*Assistant Examiner* — Erin M Cardinal
(74) *Attorney, Agent, or Firm* — Baker & Hostetler LLP (57) ABSTRACT

A single sensing probe comprising multiple, spatially separate, sensing sites is utilized to sense neural activity. The sensing probe includes multiple conductors each with multiple sensing sites in a fixed geometric arrangement. The sensing probe is configured to comprise multiple combined sensing sites in polytrode configuration. By appropriately combining the wire groupings at each combined sensing site, activity sensed from a single wire with multiple sensing sites, can be coupled with other wires to unmix signals from the spatially separate sites and leverage the power of combinatorics to maximize total recording bandwidth and single neuron/unit yield per wire and per probe.

18 Claims, 7 Drawing Sheets

Related U.S. Application Data 8, 2006, now abandoned.

(60) Provisional application No. 61/286,531, filed on Dec. 15, 2009, provisional application No. 60/715,228, filed on Sep. 8, 2005.

(56) References Cited

U.S. PATENT DOCUMENTS

| | | | |
|---|---|---|---|
| 5,311,866 A | 5/1994 | Kagan et al. | |
| 5,411,527 A | 5/1995 | Alt | |
| 5,518,836 A | 5/1996 | McCullough | |
| 5,575,810 A | 11/1996 | Swanson et al. | |
| 5,653,684 A | 8/1997 | Laptewicz et al. | |
| 5,716,391 A | 2/1998 | Grandjean | |
| 6,091,979 A * | 7/2000 | Madsen | 600/377 |
| 6,171,239 B1 | 1/2001 | Humphrey | |
| 6,315,778 B1 | 11/2001 | Gambale et al. | |
| 6,487,326 B1 | 11/2002 | Pantano et al. | |
| 6,837,886 B2 | 1/2005 | Collins et al. | |
| 7,010,356 B2 | 3/2006 | Jog et al. | |
| 7,255,695 B2 | 8/2007 | Falwell et al. | |
| 7,481,808 B2 | 1/2009 | Koyfman et al. | |
| 8,639,311 B2 * | 1/2014 | Giszter | 600/377 |
| 2002/0032462 A1 | 3/2002 | Houser et al. | |
| 2002/0113335 A1 | 8/2002 | Lobovsky et al. | |
| 2003/0137083 A1 | 7/2003 | Ko et al. | |
| 2003/0168756 A1 | 9/2003 | Balkus, Jr. et al. | |
| 2004/0181139 A1 | 9/2004 | Falwell et al. | |
| 2004/0187875 A1 | 9/2004 | He et al. | |
| 2005/0010095 A1 | 1/2005 | Stewart et al. | |
| 2005/0043894 A1 | 2/2005 | Fernandez | |
| 2005/0096647 A1 | 5/2005 | Steinke et al. | |
| 2005/0113744 A1 | 5/2005 | Donoghue et al. | |
| 2005/0124848 A1 * | 6/2005 | Holzner | 600/9 |
| 2008/0255439 A1 | 10/2008 | Tang et al. | |
| 2009/0099441 A1 | 4/2009 | Giszter et al. | |
| 2010/0198040 A1 | 8/2010 | Friedman et al. | |
| 2013/0211222 A1 | 8/2013 | Giszter | |

OTHER PUBLICATIONS

Angelopoulos, M., "Conducting polymers in microelectronics," IBM J. Res. & Dev., Jan. 2001, 45(1), 57-75.

Bohwon Kim et al., "Electrical Properties of Conductive Polymers: PET- Nanocomposites' Fibres," AUTEX Research Journal, Mar. 2004, 4(1), 9-13.

Giszter, S.F. et al., "Convergent force fields organized in the frog's spinal cord," J. Neurosci., Feb. 1993, 13(2), 467-491.

Giszter, S.F. et al., "Intraspinal microstimulation: techniques, perspectives and prospects for FES," 2000, Ch. 4, pp. 101-138 in Neural Prostheses for Restoration of Sensory and Motor Function, Ed. J.K. Chapin et al., CRC Press, Boca Raton.

Ko, F.K. et al., "Atkins and Pearce Handbook of Industrial Braids", 1989, Entire Book.

Ko, F.K. et al., "Electrospinning of Continuous carbon Nanotube-Filled Nanofiber Yarns," Adv. Mater., Jul. 17, 2003, 15(14), 1161-1165.

Ko, F.K., "Nanofiber Technology: Bridging the Gap between Nano and Macro World," Nanoengineered Nanobrous Materials, 2004, 1-18.

Li, W.-J. et al., "Electrospun Nanofibrous Structure: A Novel Scaffold for Bioengineering," J. Biomedicals Materials Research, Wiley Interscience, Mar. 25, 2002, pp. 613-621.

Norris, I. D. et al., "Electrostatic Fabrication of Ultrafine Conducting Fibers: Polyaniline/polyethylene oxide blends," Synthetic Metals, Aug. 2000, 114(2), 109-114.

Pancrazio, J.J. et al., "Toward Neurotechnology Innovation: Report from the 2005 Neural Interfaces Workshop. An NIH-Sponsored Event," Neuromodulation, Jan. 2006, 9(1), International Neuromodulation Society, 1-7.

Rathnasingham, R. et al., "Characterization of implantable microfabricated fluid delivery devices," IEEE Trans. Biomed. Eng., Jan. 2004, 51 (1), 138-145.

Rousche, P.J. et al., "A method for pneumatically inserting an array of penetrating electrodes into cortical tissue," Annals of Biomedical Engineering, 1992, 20(4), 413-422.

* cited by examiner

SENSING PROBE COMPRISING MULTIPLE, SPATIALLY SEPARATE, SENSING SITES

CROSS REFERENCE TO RELATED APPLICATIONS

The instant application is a continuation of, and claims priority to, U.S. patent application Ser. No. 12/967,878, filed Dec. 14, 2010 and now U.S. Pat. No. 8,639,311 issued Jan. 28, 2014. U.S. patent application Ser. No. 12/967,878 claims priority to U.S. Provisional patent application No. 61/286,531, filed Dec. 15, 2009. U.S. patent application Ser. No. 12/967,878 is a continuation-in-part of U.S. patent application Ser. No. 12/065,697, filed Oct. 9, 2008 and now abandoned. U.S. patent application Ser. No. 12/065,697 is a national stage application of international application number PCT/US 2006/035028, filed Sep. 8, 2006. PCT/US 2006/035028 claims priority to U.S. Provisional patent application No. 60/715,228, filed Sep. 8, 2005. U.S. patent application Ser. No. 12/967,878 is incorporated by reference herein in its entirety. U.S. provisional patent application No. 61/286,531 is incorporated by reference herein in its entirety. U.S. patent application Ser. No. 12/065,697 is incorporated by reference herein in its entirety. International application number PCT/US 2006/035028 is incorporated by reference herein in its entirety. U.S. provisional patent application No. 60/715,228 is incorporated by reference herein in its entirety.

GOVERNMENT RIGHTS

This invention was made with government support under grant number NS54894 awarded by the National Institutes of Health and grant number IIS 0827684 awarded by the National Science Foundation. The government has certain rights in the invention.

TECHNICAL FIELD

The technical field generally is related to detecting, recording, and/or causing electrical pulses in a nervous system and more specifically to a probe having multiple sensing probes for detecting, recording, and/or causing electrical pulses in a nervous system.

BACKGROUND

Polymeric fibrous materials are the fundamental building blocks of living systems. Fibers exist, for example, within all cells, such as, for example, DNA, cytoskeleton filaments, and as cellular structures of sensory cells, such as hair cells and rod cells of the eyes. Fibers also form the intracellular matrices and extracellular matrices for tissues and organs. Junctions between these excitable cells conduct electrical and chemical signals to elicit various kinds of stimulation. The signals direct normal functions of the cells such as energy storage, information storage and retrieval and processing in the cells of the nervous system, tissue regeneration, and sensing.

Current methodologies use sensing probes to detect, record, and/or stimulate these activities in the central and peripheral nervous systems. Typically, a sensing probe contains a single sensing site for measurement of electrical activity. This generally allows for low recording densities, and provides limited information or stimulation. Moreover, current materials and methods allow for only limited modulation of the physical, mechanical, and conductive properties of present sensing probes.

SUMMARY

A single sensing probe comprising multiple, spatially separate, sensing sites is utilized to sense neural activity. In an example embodiment, the sensing probe comprises microwires each with multiple sensing sites in a fixed geometric arrangement. A combined sensing site is configured such that it can comprise sensing sites from a single wire or multiple wires of the sensing probe. A sensing probe can be configured to comprise combined sensing sites in, for example, polytrode, tetrode, triode, and/or stereotrode configurations. Thus, a sensing probe can comprise, for example, sensing sites having multiple tetrode, triode, and/or stereotrode configurations. Via appropriate wire groupings of sensing sites in the probe, sensed activity from a single wire having multiple sensing sites can be coupled with other wires of the sensing probe to unmix intermittently occurring signals such as action potentials from its spatially separate sites. The combinatoric approach to unmixing signals on multiple sensing site wires described herein can increase the yield of isolated neurons per wire by up to orders of magnitude compared to conventional single site wires used in tetrode arrangements, or single wires with multiple sensing sites.

Utilizing a sensing probe comprising multiple, spatially separate, sensing sites increases the numbers of neurons and spatial extent of neurons that can be sensed using wires or wire-like conductors on a per conductor basis. Since each wire/conductor incurs a significant cost in local damage and may be underutilized in terms of its total potential bandwidth for sensings/recordings, the herein described sensing probe has enormous advantages for brain machine interface (BMI) and clinical applications. Further, each wire, by possessing multiple sensing sites, is likely at some sites to avoid intermittent inflammation problems observed in chronic implantations and thus provide useful signals.

The herein described sensing probes are suitable for implantation in vivo and otherwise. The sensing probes are sterilizable such that their use for sensing electrical potential in the body of a subject may be performed. Additionally, the sensing probes in some configurations can also be useful for the delivery of spatially weighted electrical signals or stimuli to such subjects. The sensing probes are useful in the environment of the brain or otherwise in the nervous system or muscular system of a subject (e.g., human patient, experimental animal, etc.). In an example embodiment, a sensing probe comprises a braid and has a plurality of electrical conductors. Sites on the sensing probe are defined for sensing and/or stimulation and at least some of the conductors are in electrical communication with the sites. The sensing or stimulatory sites can be caused to exist in a geometrically defined pattern and in a relatively high density. In an example embodiment, laser ablation techniques are utilized to generate precisely patterned de-insulation of sites on braids. The sensing probe can comprise any appropriate number of conductors. In an example configuration, the sensing probe comprises 48 conductors or more.

BRIEF DESCRIPTION OF THE DRAWINGS

FIG. 4 depicts partial schematic views 4A, 4B, and 4C, of exemplary embodiments of a microbraided sensing probe.

DETAILED DESCRIPTION OF ILLUSTRATIVE EMBODIMENTS

Figure 1:
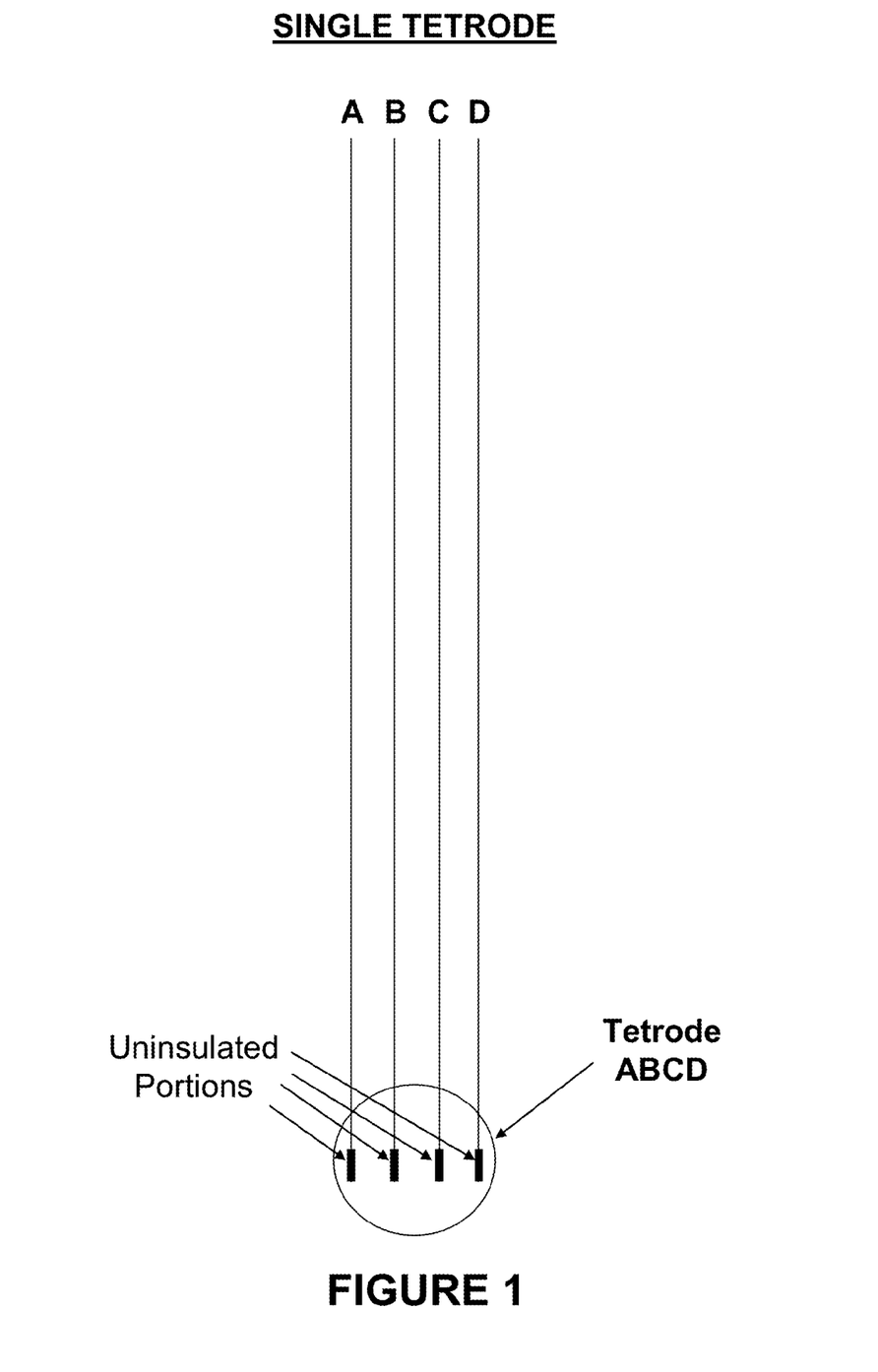
FIG. 1 depicts an example single tetrode sensing site using four wires with single sites.

A sensing probe comprising multiple, spatially separate, sensing sites utilizes wire geometry of the sensing probe to place sensing sites on several wires in close proximity. By using wires (e.g., microwires) with multiple sensing sites in fixed geometric arrangements, the throughput and bandwidth of neural activity (spiking) sensed/recorded (e.g., numbers of units and cells recorded per wire) can be maximized, while providing means for spatial localization and isolation of units using stereotrode/tetrode/polytrode techniques. By permuting the wire groupings, activity sensed from a single wire with multiple sensing sites, can be coupled with other wires to unmix signals from the spatially separate sites. This sensing probe configuration utilizes combinatorics to establish multiple tetrodes, triodes, or stereotrodes, or the like, with fewer total wires and thus with less neural trauma at an implant site. Neural data can be spatially located and isolated using real time and/or post processing techniques. Many neurons can be sensed/recorded per wire by utilizing the cross information among wires to subsequently unmix the signals. In an example embodiment, this unmixing is achieved, in part, in real time, using various signal processing (e.g., digital signal processing, DSP) and/or energy detection techniques on the multi-wire data. Post processing can be accomplished, for example, via wavelet, principal component, independent component analysis (ICA), and/or any other appropriate technique. In an example configuration, the multi-wire topology is in the form of a weave, braid, wrapping structure, or any combination thereof FIG. 1 depicts an example tetrode sensing site comprising four conductors labeled A, B, C, and D. The sensing probe comprises a single sensing site, ABCD, formed by the combination of uninsulated portions of the conductors A, B, C, and D. In an example embodiment, the uninsulated portions are plated with an adhering material. And, in an example embodiment, the adhering material may alter the sensing properties of the sensing probe. For example, the uninsulated portions can be plated, such as with gold or any appropriate material, to enhance detection and sensing of neural activity. Although, the configuration of the four conductors, A, B, C, and D, can be planar, this is not required. Thus, the configuration of the four conductors A, B, C, and D, and thus the sensing site, ABCD, can be in three dimensions.

Figure 2:
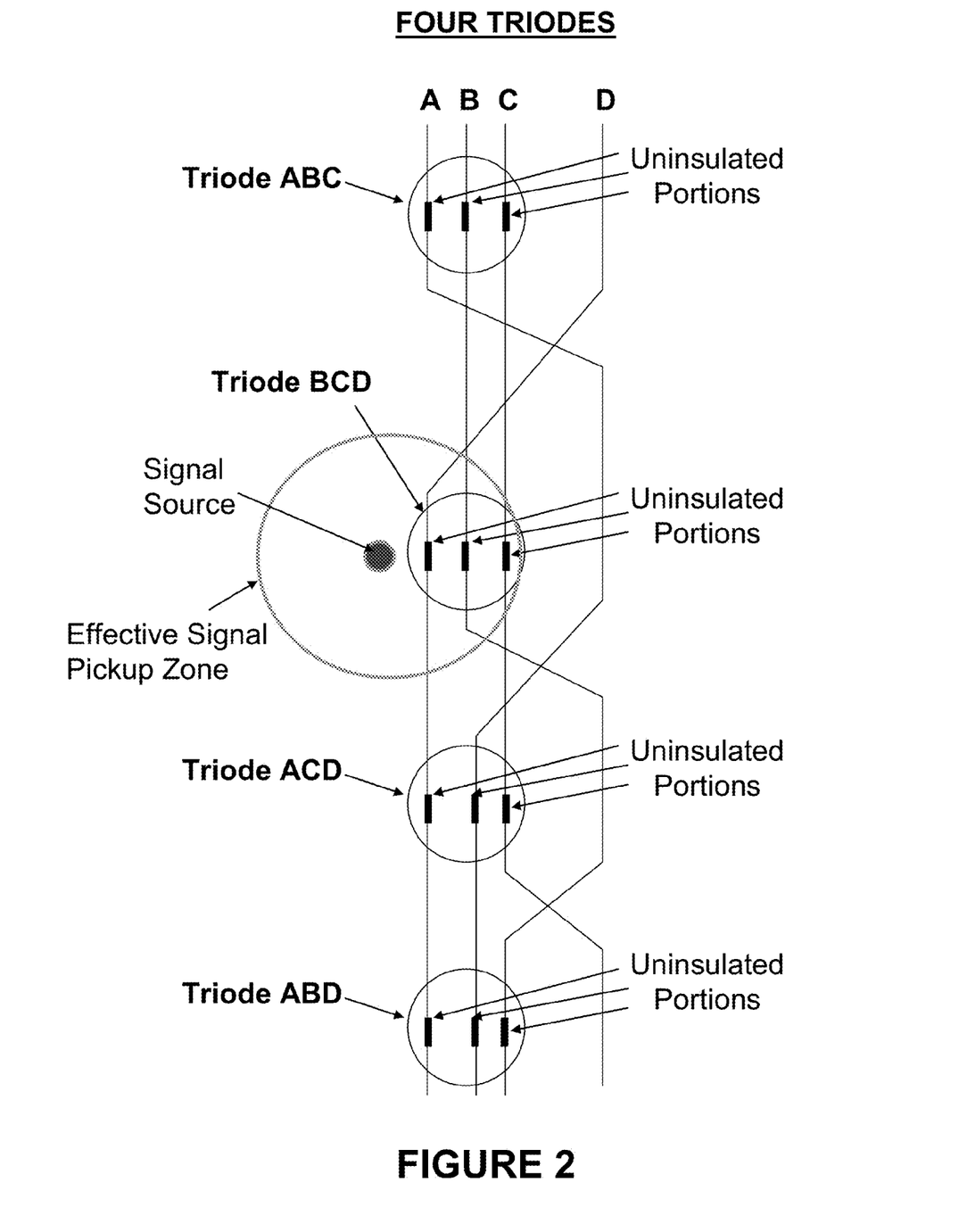
FIG. 2 depicts an example of 4 triode sensing sites using three sensing sites on each of four wires.

FIG. 2 depicts example triode sensing sites ABC, BCD, ACD, and ABD. As shown in FIG. 2, the sensing probe comprises four conductors labeled A, B, C, and D. The sensing probe comprises four combined sensing sites labeled as ABC, BCD, ACD, and ABD, each of which is formed by the combination of uninsulated portions of the three (triode) conductors, wherein no two sensing sites are formed by the same three conductors. This arrangement is formed by combined sensing sites formed from a mathematical 4 choose 3 combination. As previously described, in an example embodiment, the uninsulated portions are plated, such as with gold or any appropriate material, to enhance detection and sensing of neural activity. The configuration of the four conductors, A, B, C, and D, need not be planar. Thus, the configuration of the four conductors A, B, C, and D, and thus the sensing sites, ABC, BCD, ACD, and ABD, can be in three dimensions. As shown in FIG. 2, the triode BCD is capable of sensing a signal in the region labeled as the effective signal pickup zone. And, a signal source is depicted therein. Thus a sensing site is capable of sensing a signal within an effective zone. The zone can be a three-dimensional zone. Thus, for example, the effective signal pickup zone depicted in FIG. 2 can represent a sphere or spheroid.

Figure 3:
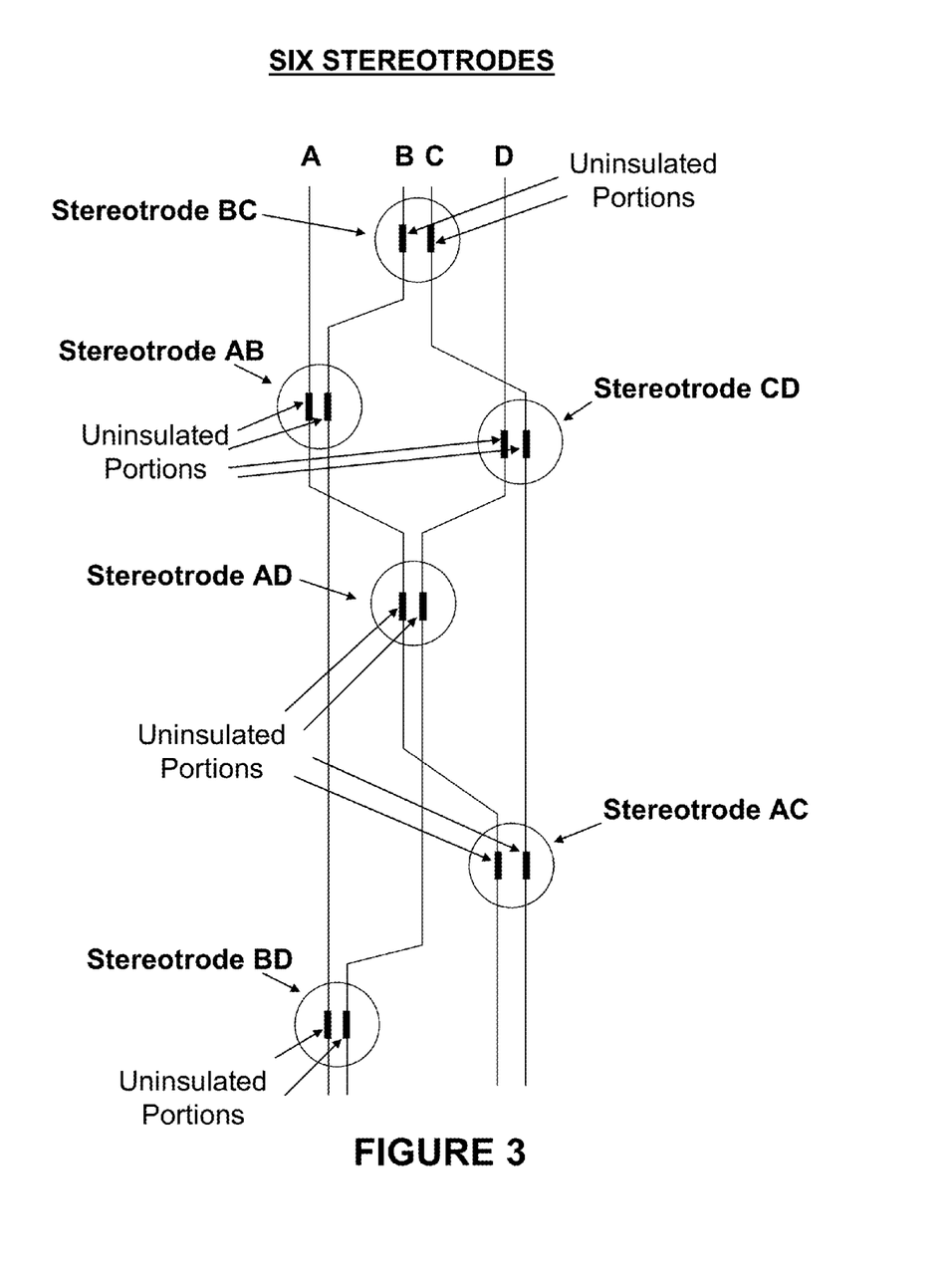
FIG. 3 depicts an example of six stereotrode sensing sites.

FIG. 3 depicts example stereotrode sensing site BC, AB, CD, AD, AC, and, BD. As shown in FIG. 3, the sensing probe comprises four conductors labeled A, B, C, and D. The sensing probe comprises six combined sensing sites labeled as BC, AB, CD, AD, AC, and, BD, each of which is formed by the combination of uninsulated portions of the two (stereotrode) conductors, wherein no two sensing sites are formed by the same two conductors. This arrangement is formed by combined sensing sites formed from a mathematical 4 choose 2 combination. As previously described, in an example embodiment, the uninsulated portions are plated, such as with gold or any appropriate material, to enhance detection and sensing of neural activity. The configuration of the four conductors, A, B, C, and D, need not be planar. Thus, the configuration of the four conductors A, B, C, and D, and thus the sensing sites, BC, AB, CD, AD, AC, and, BD, can be in three dimensions.

It is to be understood that the depiction of a sensing probe with four conductors is exemplary and not intended to be limiting. Thus, a sensing probe can comprise more or less than four conductors. For example, depending upon characteristics of the neural activity (e.g., maximum spike frequencies), mixing, and/or spatial frequencies, etc., 24, 48, or more conductors can be utilized per sensing probe. Further, sensing sites can comprise any number of conductors. For example, a sensing site can comprise a single conductor or multiple conductors forming any appropriate polytrode (e.g., tetrode, triode, stereotrode, etc.). An example of the power of this combinatoric electrode design approach is that use of 6 wires in this design framework can provide combined sensing sites that are (a) the equivalent of 20 conventional tetrodes (6 choose 4) if allowed 10 sensing sites per wire or (b) the equivalent of 6 conventional tetrode sites if allowed 4 sensing sites per wire. Conventional tetrode per wire yields are typically equivalent to microwires or about 1.3 units per wire. The combinatorics design (a) can thus be expected to yield 20×4×1.3=104 units on average and the design (b) 6×4×1.3=31 units. These are nearly 10 fold and 5 fold yield increases over the 6 wires alone with single sites on each wire.

The herein described sensing probes having multiple, spatially separate, sensing sites are useful in the sensing/recording of (or differential stimulation of) the central and peripheral nervous systems, and muscular (EMG) electrical activity. The insulated sensing probes described herein are capable of sensing (or stimulating differentially) at a plurality of sites along the dimensions of the sensing probes. In addition, the sensing probes comprise a plurality of electrically independent conductors, interwoven either to form or to be incorporated within a braid. The sensing and/or stimulating sites can be on the surface of the braid or within the braid. The nature of the braided configuration allows for sensing probes that are self-stabilizing, strong, and flexible and which have adjustable mechanical properties. Braided sensing probe designs and construction as described herein permits the fine adjustment of electrical properties of the sensing probe; dimensions of exposed tips; insulation; structural integrity; and operating environment characteristics.

The braided sensing probes can be arranged in any braided configuration. The mechanical properties of these sensing probes can be manipulated depending on the type of braided arrangement selected. In example embodiments, the braids can be tubular, for example, a "Maypole dance" arrangement or a "Chinese finger trap" arrangement. In a "Chinese finger trap" arrangement, the exertion of axial force on the braid tightens the braid. Exertion of an inward force can loosen the braid.

In other example embodiments, the braids can be flat. In yet other example embodiments, the braids can be rectangular. In still other example embodiments, the braids can comprise a figured arrangement in which the braid configuration differs along the length of the sensing probe. Both two-dimensional and three-dimensional braids are within the scope of the herein described sensing probes.

FIG. 4 depicts partial schematic views of an exemplary embodiment of a microbraided sensing probe. FIG. 4 depicts relatively simple braided sensing probes (e.g., Maypole braid) in accordance with example configurations of the sensing probe comprising multiple, spatially separate, sensing sites. For example, fibers 10 are braided together over a braiding form 12. FIG. 4A shows a conical structure for the tip of the sensing probe. It also shows sites on the conductive fibers 14 which are exposed to the environment and useful for sensing electrical potential, for achieving differential electrical stimulation, or both. In an example embodiment, these are regularly arrayed in a geometric pattern defined by the braid. In this embodiment, the braiding form may also be active. For example, the form may be a fiberoptic device, a cannula, a micropipette or other element, which is itself useful intracorporeally. FIG. 4A shows one sensing/actuation site per conductor for the sake of simplicity. It is to be understood however, that multiple sites per conductor are applicable. While in FIG. 4, each filament or fiber 10 is depicted a being a single conductor, insulated except for at the activation/sensing site, each filament or fiber can also comprise pluralities of individual conductors or other fibers, fibrils, or filaments. In such cases, increased density of conductors and actuation/sensing sites can be achieved.

FIG. 4B shows how a tubular braided sensing probe can be made by braiding fibers 10 over braiding form 12. Change in the geometry of the sensing probe can be achieved through appropriate shaping of the form, here into a pencil-like shape. It is also useful to form the braided sensing probe into a simple tubular configuration for many embodiments, whereupon use of a conical section is not made. FIG. 4C depicts a conical braiding arrangement of sensing probe tip with sensing/stimulation sites 14 arrayed generally longitudinally along the braid.

Figure 5:
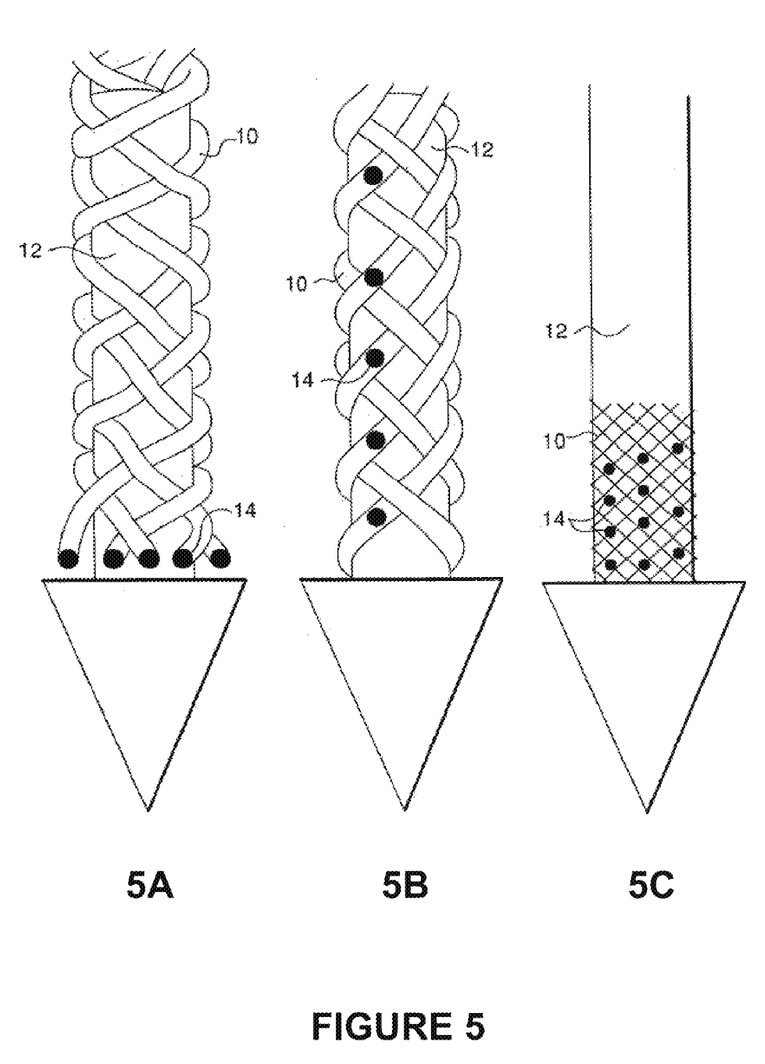
FIG. 5 depicts example sensing sites on a braided sensing probe for example embodiments 5A, 5B, and 5C.

FIG. 5 depicts sensing sites on a braided sensing probe. FIGS. 5A, 5B, and 5C show three embodiments, each generally tubular in braid structure. FIG. 5 depicts different arrangements and geometries of sensing/ stimulation sites on the braids. A single conductor can communicate with pluralities of sites or vice versa. FIG. 5 is intended to imply that the braided sensing probes can be removed from the braiding form after formation and used independently and in different configurations. Such release can be performed after insertion intracorporeally or otherwise.

Figure 6:
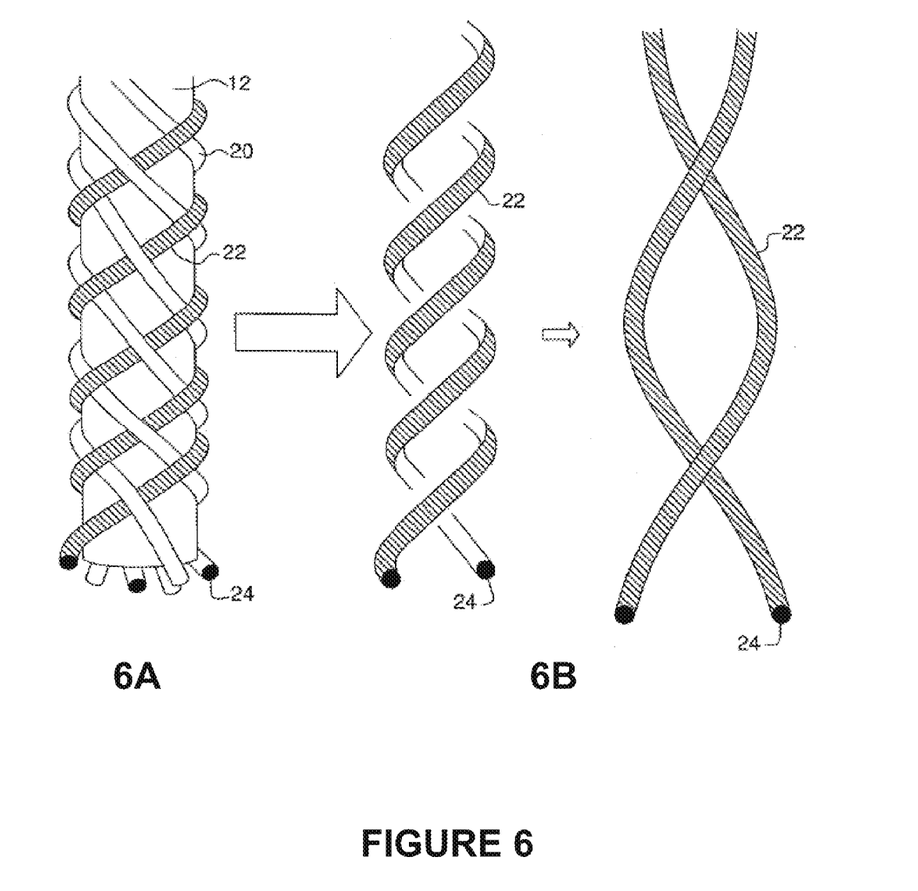
FIG. 6, including 6A and 6B, depicts certain biodegrading elements which dissolve or degrade in vivo leaving areas of exposed conductor behind on non-biodegradable elements.

FIG. 6 depicts example biodegrading elements which dissolve or degrade in vivo leaving areas of exposed conductor behind on non-biodegradable elements. FIG. 6A is of a tubular braided sensing probe comprising conducting, biologically stable filaments 22 and biologically soluble or degradable filaments 20 braided together over a form 12. As shown, the two types of fibers are braided clockwise and anticlockwise. In this case, the braided sensing probe, formed of both degradable or soluble fibers and non degradable or insoluble fibers, can be removed from the braiding form after braiding. After exposure to biological conditions or to solvent, stable filaments 22, most or all of which include conducting elements, are released and form a new geometry, here a helical pattern. FIG. 6B depicts this along with the sensing/stimulation sites 24. The geometry can further change, as shown, by relaxing, or otherwise. In this way, relative small, loosely organized conductors can be delivered to a biological situs in a relatively rigid, structured form and released to assume a relative loose, form. This arrangement permits delivery of very small sensing probe units and ones having minimal impact upon the organism into which the sensing probes have been implanted.

Figure 7:
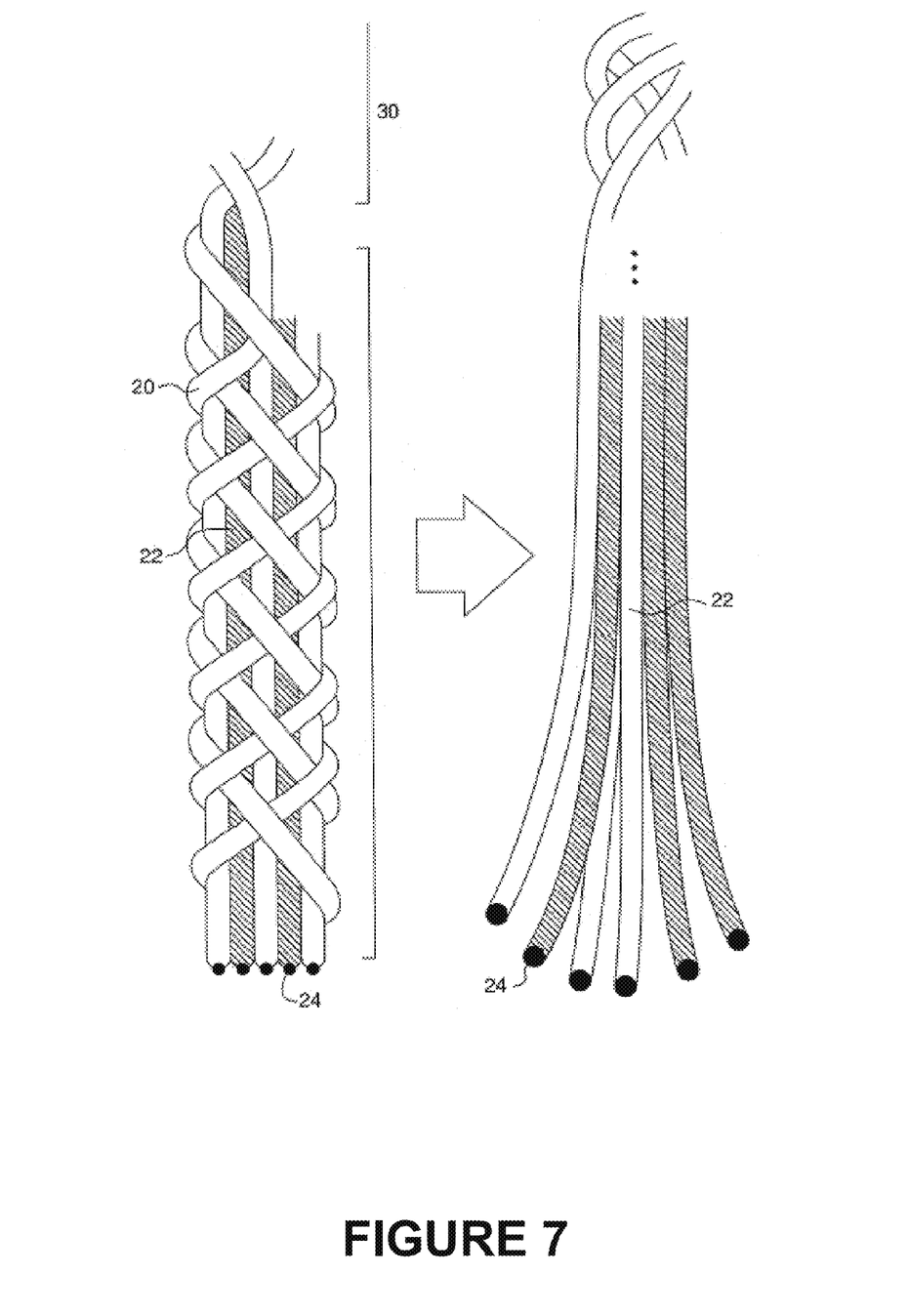
FIG. 7 depicts example conductor elements surrounded by a biodegrading braided element.

An embodiment employing soluble or degradable fibers is shown in FIG. 7. FIG. 7 depicts example conductor elements surrounded by a biodegrading braided element. Upon dissolution or degrading of the element, the conductors and/or combined sensing sites gently expand in geometry. That is, the geometric structure of conductors may expand and/or the geometric structure of the combined sensing sites may expand. A figured braid, formed of soluble or biodegradable fibers 20 surrounds conductive elements 22, such as nano or microscale insulated conductors or wires, at least an end portion of a sensing probe. Stimulation or sensing sites 24 are also shown. Here, optionally, a portion of the sensing probe 30, away from the distal end, the end intended for contact with tissue, is braided in a different fashion, protected or otherwise kept generally intact for purposes of improved handling. Perforce, the braiding of the sensing probes can change along the sensing probe's length for this and other purposes. Upon dissolution or degradation of the surrounding braid, the bundled conductors, here shown in hatching along with other, non-hatched elements, may ease apart to confer a different configuration. In some cases, improved intimacy with tissue may be had, as may a lowering of strain, within the group of bundled elements. In addition to the conductors, the elements of the bundle may include fiber optic, electronic, MEMS, OLED, or any appropriate active element.

The compliance and shape of the sensing probes described herein are alterable. These properties can be altered, for example, by the selection of the materials comprising the sensing probes. These properties can also be altered by altering the diameter of the materials comprising the sensing probes. These properties also can be altered by altering braid configuration or topology during construction or altering braid angle and relation to the supporting and embedding materials around the braid in-situ. The braided sensing probes include conductors, which can be monofilaments, multifilaments, or other forms. In certain embodiments, at least one conductor forms a part of the braided sensing probe. In others, the conductor can be laid into the braid. The conductors can comprise any number of individual conductive elements. For example, the conductors can comprise metals, such as nichrome or stainless steel. They also can comprise conductive polymers such as lithium doped polyaniline and polyethylene dioxythiophene. In some example embodiments, the conductors can comprise conductive proteins. In yet other example embodiments, the conductors can be conductive nanotubes or nanofilaments, for example, carbon nanotubes or nanowires. These materials can be microscale, nanoscale, or combinations of both microscale and nanoscale materials. In some example embodiments, the conductors can be hollow. In an example embodiment, at least one conductor has a length that is at least 100 times greater than its diameter and, in some example embodiments can be monofilaments.

The conductors can be insulated with a material such as with Teflon or Parylene C. In example embodiments, the conductors can comprise intermittent insulation along the length of the conductors, providing a plurality of sites along the length of the braid structure for use in sensing or stimulation of the central or peripheral nervous system.

In addition to comprising conductive elements, the braided sensing probes further can comprise biocompatible materials that can enhance mechanical and/or electrical properties. In example embodiments, these materials can be used to alter the compliance and/or shape of the braided sensing probes. These materials can be nanoscale, microscale, or combinations thereof For example, these fibers can have diameters ranging from about 600 nm to about 1000 μm (microscale fibers) or less than 600 nm (nanoscale fibers, under NSF definitions). These biocompatible materials also can be protein fibers or synthetic polymers. For example, in some embodiments, protein fibers such as fibroin, including Bombyx mori and spider silk, and keratin, such as wool, can be incorporated into the braids to provide mechanical strength to the braided sensing probes. In other embodiments, collagen or elastin fibers are incorporated to provide mechanical strength to the sensing probes. It also is envisioned that combinations of fibroin, keratin, collagen, and elastin can be incorporated. In certain embodiments, these materials comprise shape memory polymers or shape memory metals. These, for example, can be used to actuate braid shape changes.

Synthetic polymers also can be incorporated into the braids to enhance mechanical and/or electrical properties of the sensing probes. For instance, biocompatible poly-L-lactic acid can be electrospun into fibers with diameters ranging from about 150 nm to about 550 nm. Inclusion of poly-L-lactic acid into the braided sensing probes can improve the mechanical properties of the sensing probes by increasing the modulus. Verification of incorporation of the poly-L-lactic acid fibers into the braided sensing probes can be performed using Raman spectroscopy. Polyethylene oxide (PEO), polyaniline (PANi), and blends thereof can also be electrospun to form fibers that can be incorporated.

Certain conductive polymers having desirable mechanical properties, for example, PEDT, can also be incorporated into the braided sensing probes described herein. Other desirable polymers include, but are not limited to, polylysine, a blend of polyethylene oxide/polyaniline, polyacrylonitrile, poly(3,4-ethylenedioxythiophene)poly(styrenesulfonate), a blend of poly(3,4-ethylenedioxythiophene)/polyacrylonitrile, or polylactic-co-glycolic acid.

In some embodiments, the braided sensing probes further can comprise biodegradable materials. In such embodiments, certain biodegradable materials, for example vicryl, sucrose, dextrose, carbowax, mannose, or polyethylene glycol, can be incorporated into the braid to enhance its mechanical properties. For example, the biodegradable material might impart stiffness to the braid, facilitating the insertion of the sensing probe to the desired site. Once inserted into the nervous system, the material would then biodegrade, resulting in an in situ modification of the mechanical properties of the sensing probe. For example, once the material biodegrades, the sensing probe would usually become more flexible, and/or alter spatial shape.

In other embodiments, dissolvable, for example, materials that dissolve in solvents ex vivo, may be incorporated into the braided sensing probes. In certain embodiments, such materials could be incorporated into the sensing probes during their manufacture to provide certain mechanical properties to the sensing probes. After manufacture, the sensing probes could be immersed in a suitable solvent to dissolve the dissolvable material, thus altering the mechanical properties of the sensing probes prior to insertion at the desired situs.

Sensing probes further can comprise quantum dots. A quantum dot is a semiconductor nanostructure that confines the motion of conduction band electrons in three spatial directions. Sensing probes also can comprise microelectromechanical systems within the braided structure. In example embodiments, the sensing probes form at least one triode. In other example embodiments, the sensing probes form at least one tetrode. In still other example embodiments, sensing probes form at least one polytrode. Sensing probes described herein also can exist as part of a composite structure.

Sensing probes of the present invention may also comprise a plurality of individual braided sensing probes. In some embodiments, several braided sensing probes can be assembled to form an array of braided sensing probes arranged in rows and/or columns like tines of combs. Preferably, the sensing probes can be assembled to form a cuff sensing probe suitable for placement around a nerve.

It is also envisioned that sensing probes may further comprise cannulas, catheters, or other surgical devices through which fluids could be delivered to the situs of the sensing probe.

In certain embodiments, a plurality of independent conductors can be "laid into" the braid. A conductor which is "laid into" a braid is one which is ensnared by the braid, but which does not form part of the braid itself. In other embodiments, these conductors can be modified by exposing at least some of them to the environment. Preferably, the compliance and/or shape of these braided sensing probes can be altered in a controlled fashion.

Sensing probes can be formed by braiding a plurality of fibers onto, over, or within a braiding form, wherein some of these fibers are independently conductive. A braiding form is any material upon which materials can be braided. All braiding configurations are envisioned. The fibers can be modified by exposing them to the environment. This exposure can take place along the length of the braided sensing probe, at a plurality of sites. The fibers can be biocompatible and able to withstand sterilization conditions.

In some example embodiments, the braiding form remains within the braided sensing probe. In some embodiments, the braiding form is inert to environmental conditions. In other example embodiments, the braiding form is biodegradable or dissolvable. In still other example embodiments, the braiding form has shape memory properties. In yet other example embodiments, the braiding form is conductive. For example, the braiding form can comprise a fiberoptic material such as quartz. The braiding form can also comprise a metal such as tungsten. In some embodiments, the braiding form comprises glass. In other embodiments, the compliance of the braiding form is alterable.

In an example embodiment, the braided structure is affixed to the braiding form. For example, the braided structure can be affixed to the braiding form with an adhesive such as cyanoacrylate. In some embodiments, the braided structure can be affixed to the braiding form with biodegradable or dissolvable materials, for example, mannose.

In one embodiment, the braiding form can comprise a fiberoptic fiber. Such embodiments can be useful in, for example, focal uncaging of caged neurotransmitters. In example embodiments, the fiberoptic fiber is sputter coated with a metal, for example, platinum, for recording. Preferably, the fiberoptic is insulated. Exemplary examples of insulating materials are Parylene-C and PTFE.

In one example embodiment, the braiding form is a fiberoptic quartz fiber, preferably 50 μm. This fiber is pulled to a fine tip, for example 10 μm. Caged compounds can be delivered into the cord via a tubular braid or a cannula of carbon nanofibers or other very fine fibers from different polymers. The nanofibers are braided to form a 30 μm shaft and coated with medical grade silicon rubber. A guide provides the cannula stiffness for insertion into the spinal cord, and can be removed once the cannula is in place. The cannula left in place is highly flexible, thus limiting damage to the spinal cord. The conductive filaments can be spaced precisely and they can be separated by nonconductive filaments of finer diameter.

To assure precision fiber placement and facilitate the manipulation of very delicate micron level filaments, a computer aided design and manufacturing system capable of nanoscale and microscale fiber placement can be used. For this system, a geometric design algorithm can be developed and the information translated to machine instruction code. To provide sufficient structural stability, it is preferred that a computer controlled microbraiding system be used. Such a system is extendible to nanoscale levels by the use of a nanomanipulator system such as the Zyvex L100 nanomanipulator capable of operating in an SEM chamber.

In addition to use in neurological contexts, the sensing probes also can be used in medical contexts apart from the brain or nervous system such as in the delivery of stimulatory signals for tissue regrowth, for stimulation of other sorts, and in ex vivo applications. The present sensing probes can find use in industrial applications as well, especially where pluralities of sensing or stimulatory sites are required in predefined, spatially organized fashions.

The braided sensing probes can feature any braided structure, tubular, flat, figured, or more complex braids being suitable and known per se. Braided structures which may have their geometries altered in preselected and predictable ways also are featured. Employment of different patterns of sensing/stimulation sites can be performed with one pattern being used for sensing and another for stimulation. Alternatively the patterns may overlap. It is not necessary that one braided sensing probe perform both sensing and stimulation, however.

The conductors can form part of the braid, may be "laid into" the braid, or both. In some embodiments, some or all of the conductors are monofilaments. In some embodiments, at least some of the conductors have lengths which are at least about 100 times their diameters. In other embodiments, conductors have average diameters on the order of from about one μm to about 50 μm. In others, conductor average diameters on the order of from about 0.1 μm to about 1 μm are preferred. As will be appreciated, control of conductor size and geometry permits the careful control of the geometry and spacing of the sites of stimulation and or sensing.

In an example embodiment, substantially all of the conductors have average diameters less than about 50 μm.

The conductors can be metal, conductive polymer, conductive protein, or conductive nanostructure, such as nanotubes or nanofilaments. All these materials are known per se. In some embodiments, doped conjugated polymers such as polyanaline are employed in filamentous form. Carbon nanotubes are featured as conductive elements on other embodiments.

For some applications, use of materials which have geometric "memory" such as memory metals or memory polymers may be useful as the same may permit improved contact with certain body parts, conformation to complex structures and the like. The conductors are insulated from each other and from the environment. Insulative materials such as PTFE, parylene-C or other otherwise inert materials are useful.

Coating of some or all of the conductors or other portions of the sensing probe also can be achieved to good effect. Coating with metals, such as gold, platinum, silver, iridium, other metals or combinations thereof may find use in some applications. Sputtering is a convenient way of achieving such coating although other means also can be employed, such as reductive deposition and the like.

The braided sensing probes also can comprise one or more optical elements, such as fiber optic strands or cables. Such inclusion can facilitate placement of the sensing probe or can be used in monitoring either the sensing probe or a body state in a subject. This is useful in conjunction with cannulas, catheters, probes, or other surgical or medical devices. For example, application of a sensing probe on or with a surgical probe facilitates the sensing of electrical potential, pH, or any of a number of body states such as glucose concentration, viscosity, or other properties adjacent the probe. Pluralities of sensing probes can be arrayed on a single instrument either of the same or of different constitution.

Other active elements can be included in braided sensing probes. Thus, quantum dots can be arrayed within such sensing probes to report upon one or more body states in organisms or tissues into which the sensing probes are introduced. The conductors can be used to transfer signals from the quantum dots to a sensing or recording device for interpretation and storage. Circuits, chips, electronic elements such as triodes, diodes, tetrodes and the like, MEMS and other elements known per se, may also be included in this way. The use of partially or wholly hollow of shaped conductors may benefit these embodiments and other aspects of the invention. Light emitting diodes, especially those coupled to a body state sensing system are particularly useful, especially when arrayed consonant with the pattern of sites for sensing or stimulation.

In one class of embodiments, braided sensing probes are constructed including one or more biodegradable or dissolvable elements. If some or all of the braided materials can be caused to be completely or partially dissolved or degraded in a predictable fashion, usually after implantation, the remaining elements of the sensing probe may exhibit beneficial properties or results. For example, dissolution of a braid may affect the exposure of sensing/stimulation sites on conductors forming part of a sensing probe. Additionally, a dissolved or degraded braid may liberate conductors to assume an altered or different shape or geometry. In such a way, particularly intimate contact between conductor and tissue may be achieved. Removal of degradable material may also facilitate the long term placement of sensing probes by diminishing the overall size of sensing probes and by possibly improving their biocompatibility.

The biodegradable materials useful for these embodiments include vicryl, sucrose, dextrose, carbowax, mannose, polyethylene glycols, polylactic acids, polyvinyl alcohols, and any other material which can be used to elaborate braided sensing probes in accordance herewith and which, at a predictable point in time or in a predictable environment, degrade or dissolve to give rise to an altered, but useful sensing probe.

While a sensing probe comprising multiple, spatially separate, sensing sites has been described in connection with the various embodiments of the various figures, it is to be understood that other similar embodiments can be used or modifications and additions can be made to the described embodiment for a sensing probe comprising multiple, spatially separate, sensing sites without deviating therefrom. Therefore, a sensing probe comprising multiple, spatially separate, sensing sites should not be limited to any single embodiment, but rather should be construed in breadth and scope in accordance with the appended claims.

What is claimed:

1. A method comprising:
    detecting signals via a sensing probe comprising a plurality of electrical conductors, wherein each conductor of the plurality of electrical conductors comprises a plurality of sensing sites, spatially separate combined sensing sites are formed from the plurality of sensing sites by proximate portions of multiple electrical conductors of the plurality of electrical conductors, and no two combined sensing sites are formed by a same combination of electrical conductors, and wherein the detected signals are indicative of neural activity; and
    combinatorially unmixing the detected signals to determine a source of the neural activity, wherein a configuration of the plurality of electrical conductors of the sensing probe is application configurable.

2. The method of claim 1, wherein the plurality of electrical conductors is configurable in situ.

3. The method of claim 1, wherein a mechanical property of the sensing probe is adjustable in situ.

4. The method of claim 1, further comprising:
    configuring proximate portions of all electrical conductors of the plurality of electrical conductors to form at least one combined sensing site of the combined sensing sites.

5. The method of claim 1, wherein:
    at least one combined sensing site of the plurality of combined sensing sites comprises a polytrode electrode.

6. The method of claim 1, wherein at least one combined sensing site of the plurality of combined sensing sites comprises a tetrode electrode.

7. The method of claim 1, wherein at least one combined sensing site of the plurality of combined sensing sites comprises a triode electrode.

8. The method of claim 1, wherein at least one combined sensing site of the plurality of combined sensing sites comprises a stereotrode electrode.

9. The method of claim 1, wherein the plurality of electrical conductors is formed as a braid.

10. The method of claim 1, wherein the sensing probe comprises a biodegradable element surrounding at least a portion of the plurality of electrical conductors.

11. The method of claim 10, wherein responsive to degradation of the biodegradable element, a geometric structure of the plurality of electrical conductors varies.

12. A method comprising:
    detecting signals via a sensing probe comprising a plurality of electrical conductors, wherein each conductor of the plurality of electrical conductors comprises a plurality of sensing sites, spatially separate combined sensing sites are formed from the plurality of sensing sites by proximate portions of multiple electrical conductors of the plurality of electrical conductors, and no two combined sensing sites are formed by a same combination of electrical conductors, and wherein the detected signals are indicative of neural activity; and
    combinatorially unmixing the detected signals to determine a source of the neural activity, wherein a mechanical property of the sensing probe is application adjustable.

13. The method of claim 12, wherein the mechanical property of the sensing probe is adjustable in situ.

14. The method of claim 12, wherein the plurality of electrical conductors is configurable in situ.

15. The method of claim 12, further comprising:
    configuring proximate portions of all electrical conductors of the plurality of electrical conductors to form at least one combined sensing site of the combined sensing sites.

16. The method of claim 12, wherein:
    at least one combined sensing site of the plurality of combined sensing sites comprises at least one of:
    a tetrode electrode;
    a triode electrode; or
    a stereotrode electrode.

17. The method of claim 12, wherein the sensing probe comprises a biodegradable element surrounding at least a portion of the plurality of electrical conductors.

18. The method of claim 17, wherein responsive to degradation of the biodegradable element, a geometric structure of the plurality of electrical conductors varies.

* * * * *